United States Patent [19]

Tarjan

[11] Patent Number: 4,787,389

[45] Date of Patent: Nov. 29, 1988

[54] USING AN IMPLANTABLE ANTITACHYCARDIA DEFIBRILLATOR CIRCUIT

[75] Inventor: Peter P. Tarjan, Miami, Fla.

[73] Assignee: TNC Medical Devices Pte. Ltd., Miami, Fla.

[21] Appl. No.: 74,092

[22] Filed: Jul. 16, 1987

[51] Int. Cl.[4] .............................................. A61N 1/00
[52] U.S. Cl. ......................... 128/419 PG; 128/419 D
[58] Field of Search ......... 128/419 PG, 419 D, 419 P

[56] References Cited

U.S. PATENT DOCUMENTS

| | | | |
|---|---|---|---|
| 3,857,398 | 12/1974 | Rubin | 128/419 D |
| 4,475,551 | 10/1984 | Langer et al. | 128/419 D |
| 4,641,656 | 2/1987 | Smits | 128/419 D |
| 4,693,253 | 9/1987 | Adams | 128/419 D |

OTHER PUBLICATIONS

Winkle, "The Implantable Defibrillator in Ventricular Arrhythmias", *Hospital Practice*, pp. 149-165 (Mar. 1983).

*Primary Examiner*—Francis Jaworski
*Assistant Examiner*—George Manuel
*Attorney, Agent, or Firm*—George H. Gerstman

[57] ABSTRACT

A cardiac stimulation apparatus is provided which includes an implantable cardiac pacer 10 having an antitachycardia circuit 12 and an implantable defibrillator circuit 58. The patient's electrical heart rate is sensed and if the heart rate exceeds a predetermined threshold, the antitachycardia circuit 12 is activated. If the antitachycardia circuit 12 fails to lower the heart rate to below a selected rate, the defibrillator circuit 58 is activated. A coded pulse train is transmitted between the pacer 10 and the defibrillator circuit 58 for isolating the pacer 10 from the defibrillator circuit 58 during operation of the defibrillator circuit 58.

15 Claims, 3 Drawing Sheets

USING AN IMPLANTABLE ANTITACHYCARDIA DEFIBRILLATOR CIRCUIT

FIELD OF THE INVENTION

The present invention concerns a novel apparatus and method for cardiac stimulation.

BACKGROUND OF THE INVENTION

Certain patients have cardiac rhythm disturbances in which contractions of either the atria or the ventricles or both occur at a rate that is so rapid that the cardiac patient finds it intolerable. Such rapid rhythm disturbances are designated as tacharrhythmias. In some of the patients who experience tacharrhythmias, the arrhythmias can degenerate into fibrillation. Fibrillation is chaotic electrical activity of either the atria or the ventricles which does not result in coordinated cardiac contractions, with disturbances of blood flow occurring. Death can be the outcome of ventricular fibrillation. The tacharrhythmias can result in a syncope.

In both tachycardia and in fibrillation, transthoracic cardioversion-defibrillation can be applied using high energy shocks, for example, 400 joules or less. In the case of tachycardia, the arrhythmia is converted to a slower, more tolerable rate. In defibrillation, the chaotic, non-coordinated electrical activity usually becomes organized, coordinated and at a tolerable rate.

Although such patients are usually on medication to control the arrhythmias, in some instances there is a medication failure. Implantable cardiac pacers have been developed specifically to bring the tachycardias under control. In addition, an implantable defibrillator has been developed to break the chaotic electrical activity found in fibrillation.

In one example of an antitachycardia implantable cardiac pacer, the automatic antitachycardia mechanism is activated only when the pacer's tachycardia threshold is exceeded. The tachycardia threshold is exceeded when each interval between a certain number of successive sensed events is shorter than the programmed value of the interval. One of five programmable antitachycardia mechanisms is activated when the tachycardia threshold is exceeded. These mechanisms include programmed burst, burst rate scanning, automatic overdrive, programmed critically timed pulses and critically timed scanning. Many others are possible. Further, the number of attempts to control the tachycardia can be programmed. This antitachycardia implantable cardiac pacer, in the absence of a tachycardia, can also function, dependent upon lead placement, as a conventional programmable atrial and/or ventricular inhibited cardiac pacer with programmable rate, output, etc.

An implantable cardiac defibrillator functions solely to break or convert fibrillation into a more normal rhythm. The defibrillator senses the electrical activity of the ventricles. If the rate of electrical activity exceeds some value, that is preset during manufacture, the defibrillator will emit a pulse of approximately 25 joules. If the pulse is ineffective, a second and a third, if needed, are delivered.

The implantable defibrillator operates in a different manner than the antitachycardia mechanism of the pacer. For example, the implantable defibrillator can classify a tachycardia whose rate is slightly higher than the manufacturer's set fibrillation detection rate, and the defibrillator then emits a high energy pulse.

Implanting both the cardiac pacer and the defibrillator circuit in the same patient is feasible only if the antitachycardia implantable cardiac pacer is protected against the high energy pulse or pulses delivered to the heart by the implantable defibrillator, and if the implantable defibrillator is not triggered when the antitachycardia pacer is operating in its antitachycardia mode. It is desirable that the implantable defibrillator be triggered only after the antitachycardia circuit has been unsuccessful in several successive attempts to bring the arrhythmia under control.

It is thus desirable to provide means for circuit protection and tissue protection during attempts to defibrillate the ventricles, and to provide means for actuating the implantable defibrillator if the tachycardia or arrhythmia is not brought under control by the antitachycardia circuit.

It is desirable that once the arrhythmia is brought under control, the cardiac pacer with its antitachycardia circuit be reactivated to resume monitoring of the heart.

It is, therefore, an object of the invention to provide a novel cardiac stimulation apparatus and method in which a cardiac pacer having an antitachycardia circuit and a defibrillation circuit are used cooperatively to control tacharrhythmias.

Another object of the present invention is to provide a cardiac stimulation apparatus that is relatively simple in construction and efficient to manufacture.

Other objects and advantages of the present invention will become apparent as the description proceeds.

SUMMARY OF THE INVENTION

In accordance with the present invention, a cardiac stimulation apparatus is provided which includes an implantable cardiac pacer having an antitachycardia circuit and also includes an implantable defibrillator circuit. Energy source means are provided for the pacer and the defibrillation circuit. First means are provided for connecting the pacer to a patient's heart and second means are provided for connecting the defibrillator circuit to the patient's heart. Means are provided for sensing the patient's electrical heart rate and switching means are coupled to the first connecting means and the second connecting means. The switching means are operative for isolating the cardiac pacer from the defibrillator circuit during operation of the defibrillator circuit.

In the illustrative embodiment, means are responsive to the electrical heart rate sensing means for activating the antitachycardia circuit if the electrical heart rate exceeds a predetermined threshold. Means are provided for activating the defibrillator circuit if the antitachycardia circuit fails to lower the electrical heart rate to below a selected rate.

In the illustrative embodiment, signals in the form of a coded pulse train are transmitted between the pacer and the defibrillator circuit for controlling the switching means. The pulse train is transmitted into the patient's tissue via the connecting means.

In accordance with the method of the present invention, an implantable cardiac pacer having an antitachycardia circuit is provided. An implantable defibrillator circuit is provided. Energy is provided for the pacer and the defibrillator circuit and both the pacer and the defibrillator circuit are connected to the patient's heart.

The patient's electrical heart rate is sensed and, if the rate of electrical heart cycles exceeds a predetermined amount, then the antitachycardia circuit is activated. If the antitachycardia circuit fails to lower the electrical heart rate to below a selected rate, then the antitachycardia circuit is isolated from the defibrillator circuit and thereafter the defibrillator circuit is activated.

In the illustrative embodiment, the isolating step comprises the step of providing signals between the pacer and the defibrillator circuit to control the switching means. Means are provided for telemetering the signal to the defibrillator circuit if the antitachycardia circuit fails to lower the electrical heart rate rate below a selected amount.

A more detailed explanation of the invention is provided in the description and claims, and is illustrated in the accompanying drawings.

DESCRIPTION OF THE ILLUSTRATIVE EMBODIMENT

Figure 1:
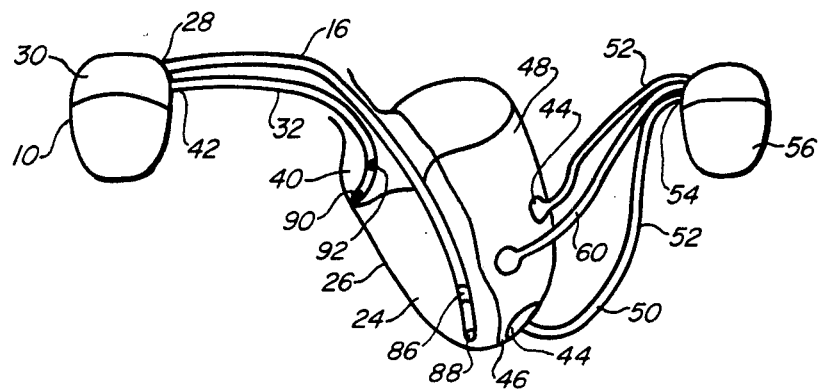
FIG. 1 is a diagrammatic view of a cardiac stimulation apparatus constructed in accordance with the principles of the present invention.
Figure 2:
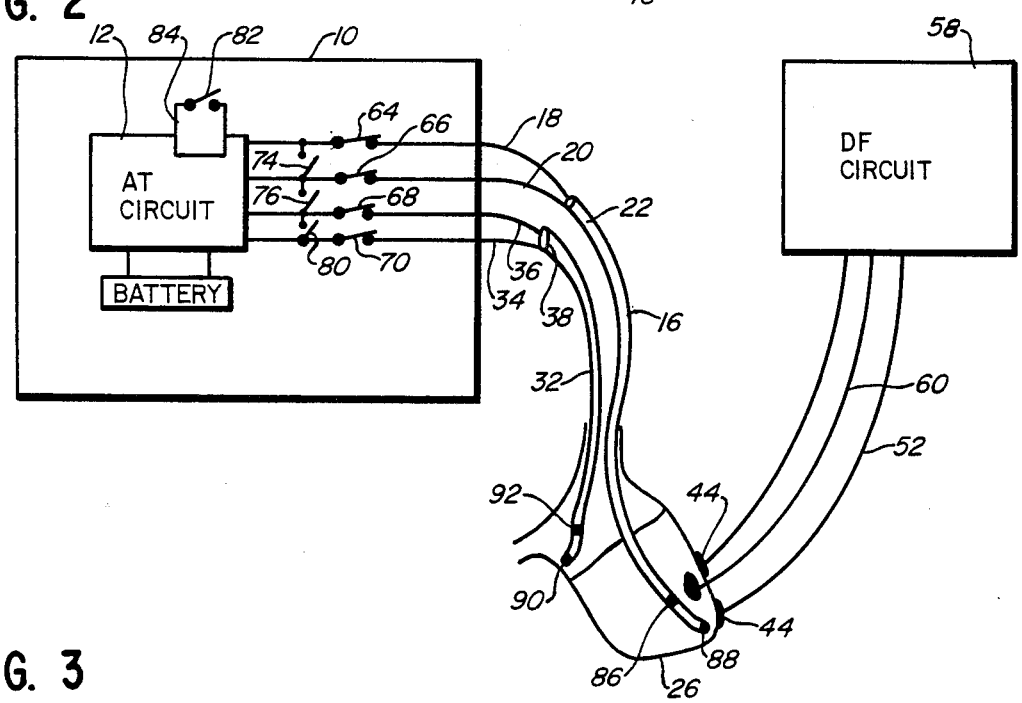
FIG. 2 is a diagrammatic representation of a switching circuit constructed in accordance with the principles of the present invention, during operation of the implantable antitachycardia circuit.

Referring to FIGS. 1 and 2, an implantable cardiac pacer 10 is illustrated containing an antitachycardia circuit 12 and a power source 14 for both the conventional pacing circuit and the antitachycardia circuit 12. A bipolar lead 16 with two conductor wires 18, 20 insulated in a sheath 22 of a biocompatible material, such as polyurethane, is placed in an appropriate vein and is advanced to the ventricle 24 of the heart 26. The proximal end 28 is connected to the cardiac pacer 10 via the connector 30. The connector 30 contains the ventricular connector blocks (not shown) into which the proximal end 28 is inserted. This connector block is connected to the ventricular circuitry and power 14 source of the cardiac pacer.

Pacer 10 may be a single chamber pacer or a dual chamber pacer. If a dual chamber pacer is used, a second bipolar lead 32 with two conductor wires 34, 36 insulated in a sheath 38 of biocompatible material, such as polyurethane, is placed in an appropriate vein and advanced to the atrium 40 of the heart 26. The proximal end 42 is connected to the cardiac pacer 10 via the neck 30. The neck 30 contains the atrial connector block (not shown) into which the proximal end 42 is inserted. As in the ventricular portion of the cardiac pacer 10, the atrial connector block is in electrical continuity with the atrial circuitry and the cardiac pacer's power supply 14.

Using a surgical approach, electrodes 44 with surface areas of approximately 10 cm$^2$ are sutured onto the apex 46 of the left ventricle 48 or some other suitable location on the heart. The conductor wires are in electrical continuity with the electrodes 44 and are contained in an insulating sheath 50. The electrodes 44, connector wires and sheaths comprise the defibrillating leads 52. The proximal ends 54 of the defibrillatory leads 52 are connected to an implantable defibrillator 56 which contains the defibrillator circuit 58. A third lead with its electrode 62 is sutured to the left ventricle 48. This lead 60 is also connected to the implantable defibrillator 56 and is generally utilized to sense or detect electrical activity generated either by the ventricle 26 or by the implanted cardiac pacer 10.

Associated with the implantable cardiac pacer 10 and its antitachycardia circuit 12 are low resistance bilateral switches 64, 66, 68, 70, 74, 76, 80 shown in FIG. 2. An additional low resistance bilateral switch 82 is associated with a telemetry coil 84 which transmits, on request, information stored in the cardiac pacer 10 to a receiving instrument located externally.

During normal operation of the cardiac pacer 10 either in its conventional mode as a dual chamber pacer or ventricular inhibited pacer or in its antitachycardia mode, switches 64, 66, 68, 70 are closed (FIG. 2) establishing electrical continuity from the pacer 10 to the electrodes 86, 88 of the ventricular lead 16 and to the electrodes 90, 92 of the atrial lead 32. Switches 74, 76, 80, 82 are open thereby interrupting the current pathway.

When the pacer 10 is programmed to an automatic antitachycardia mechanism, the pacer 10 will deliver the preset stimulus pattern only after sensing a tachycardia above the programmed tachycardia threshold rate and duration. The antitachycardia mechanisms include but are not limited to programmed burst, burst rate scanning, automatic overdrive, programmed critically timed pulses and critically timed scanning, any one of which can be chosen by external programming. Further, the number of times (N) that any one of the antitachycardia mechanisms can be applied to the heart to control the tachyarrhythmia is also programmable.

When the pacer 10 is in the antitachycardia mode and has delivered the programmed number of the chosen antitachycardia mode, a coded series of pulses is sent from the pacer 10 through the lead 16 and into the tissue through electrodes 86, 88. This coded pulse train is detected by the electrodes 62 and transmitted to the defibrillator circuit 58. The circuit 58 may monitor the arrhythmia, in some implantable defibrillators. In either instance, prior to delivering a high energy pulse of about 15 to 30 joules, the defibrillator circuit transmits a uniquely coded pulse train to the tissue. This uniquely coded pulse train is detected by electrodes 86, 88 or by electrodes 90, 92 and is transmitted to the cardiac pacer 10.

In response to the coded pulse train from the defibrillator 58, switches 64, 66, 68, 70 open and switches 74, 76, 80, 82 close. The implantable defibrillator 58 delivers a high energy (15–30 joules) pulse to the heart 26. Only a small amount of current is shunted through leads 16, 32 during this pulse, resulting in minimal tissue damage at electrodes 90, 92, 86, 88. Further, the input and output of the cardiac pacer are connected together so the current does not enter the pacer to damage the circuits.

In this defibrillator which monitors the ventricular electrical activity, a determination is made by the implantable defibrillator if the abnormally high rates have been controlled. If not, a second, high pulse is delivered with the heart being monitored for arrhythmia. The number of such high energy pulses which the defibrillator can deliver is limited by the power supply and can be up to one hundred.

The switches 74, 76, 80, 82 remain closed and switches 64, 66, 68, 70 remain open for a short period of time, usually one second before reversing their position to allow the implantable cardiac pacer 10 to resume monitoring.

Figure 4:
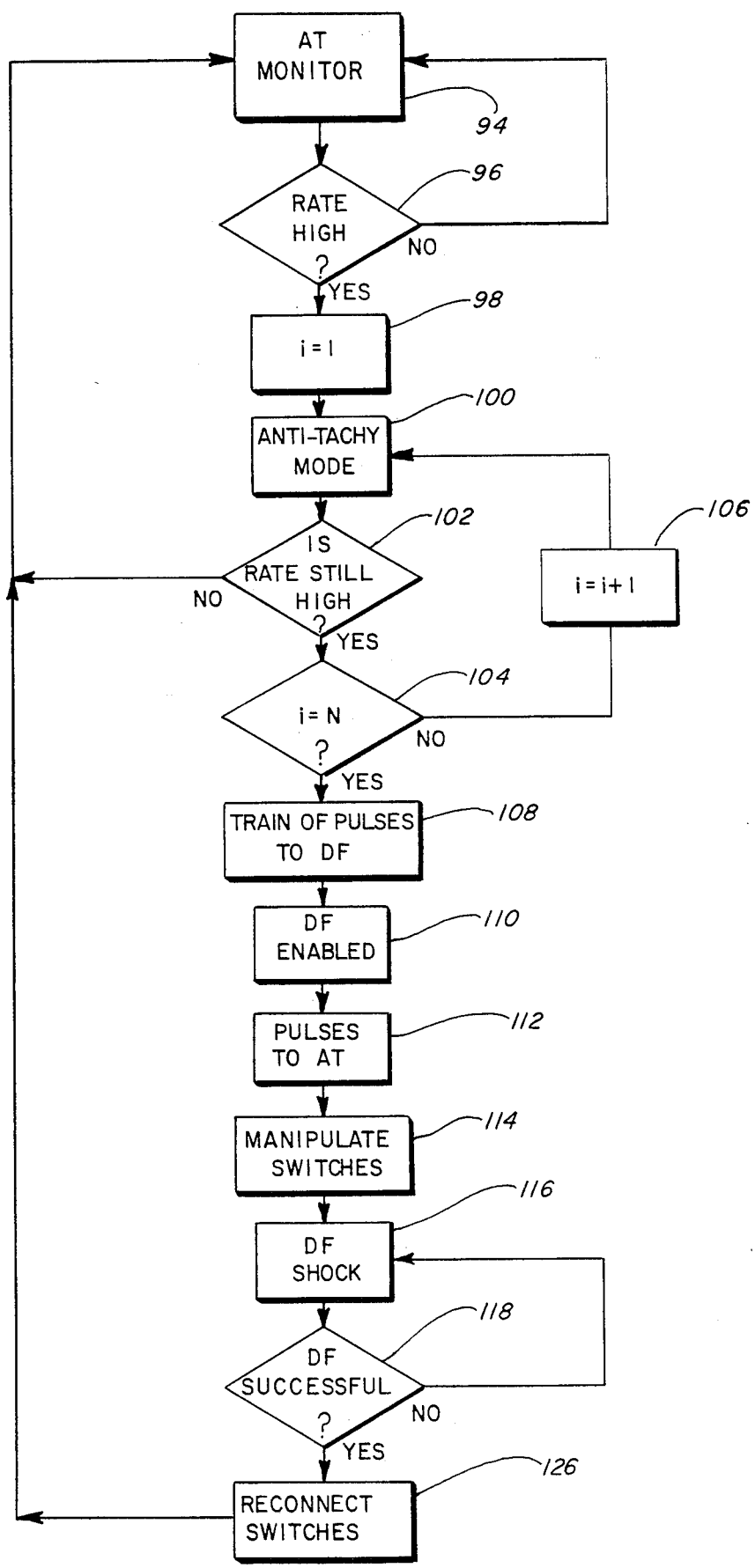
FIG. 4 is a flow chart illustrating the functional steps in the operation of a cardiac stimulation apparatus and method according to the principles of the present invention.

Referring to the flow chart of FIG. 4, the cardiac pacer monitors intervals between electrical heart cycles for an interval which is shorter than the tachycardia threshold (96) of the cardiac pacer. If this threshold is not exceeded, the pacer continues to monitor. When the threshold is exceeded and the presence of a tachycardia is affirmed, then a counter is incremented by one (98), and the pacer enters the antitachycardia mode (100) by activating the programmed antitachycardia mechanism. If this mechanism is successful, the pacer resumes monitoring (94). If the rate is still above the pacer's programmed tachycardia threshold (102) and the number of times (N) that the antitachycardia mechanism programmed into the pacer has not been attained (104), the counter is incremented by one (106) and steps 100, 102, 104 and 106 are repeated until the counter is at N, the programmed number of times the antitachycardia mechanism is repeated.

Figure 3:
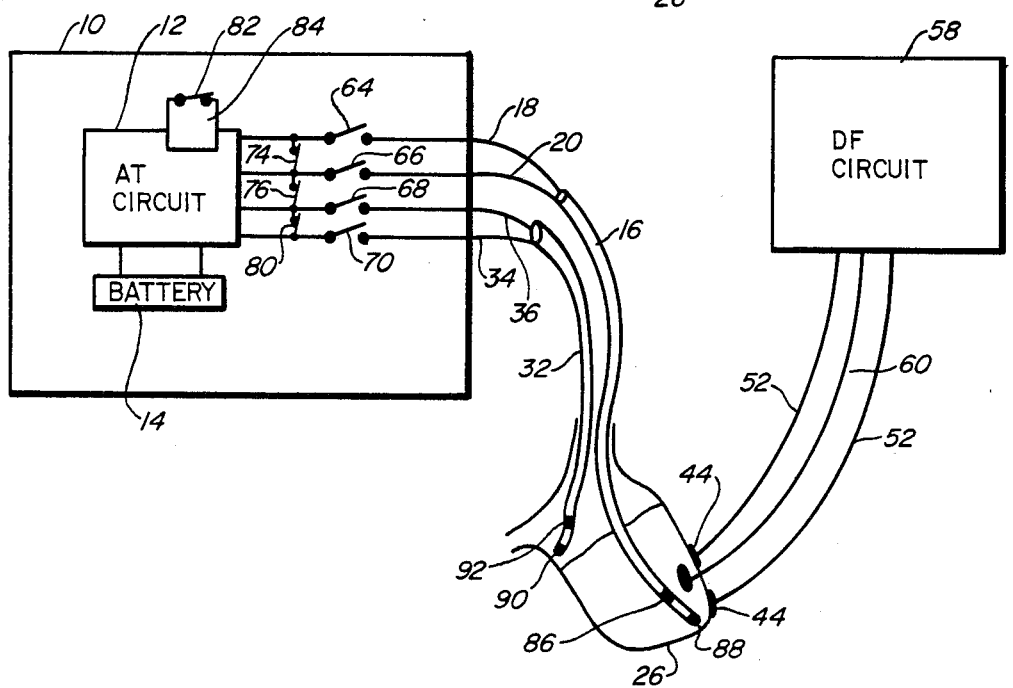
FIG. 3 is a diagrammatic representation of the switching circuit of FIG. 2 during operation of the implantable defibrillator.

When N has been attained, the cardiac pacer delivers a uniquely coded train of pulses (108) via the tissue to the defibrillator, activating the defibrillator (110). The defibrillator delivers a coded pulse train (112) to the cardiac pacer at which point the switches are manipulated to the position illustrated in FIG. 3 (114). The defibrillator issues a shock (116) and determines if this shock is successful (118). If not, a second shock is delivered to the heart. Steps 116, 118 are repeated until arrhythmia is controlled or insufficient power remains in the power source of the defibrillator. When the arrhythmia is controlled, the switches are reconnected (120) to resume monitoring of the heart.

Figure 5:
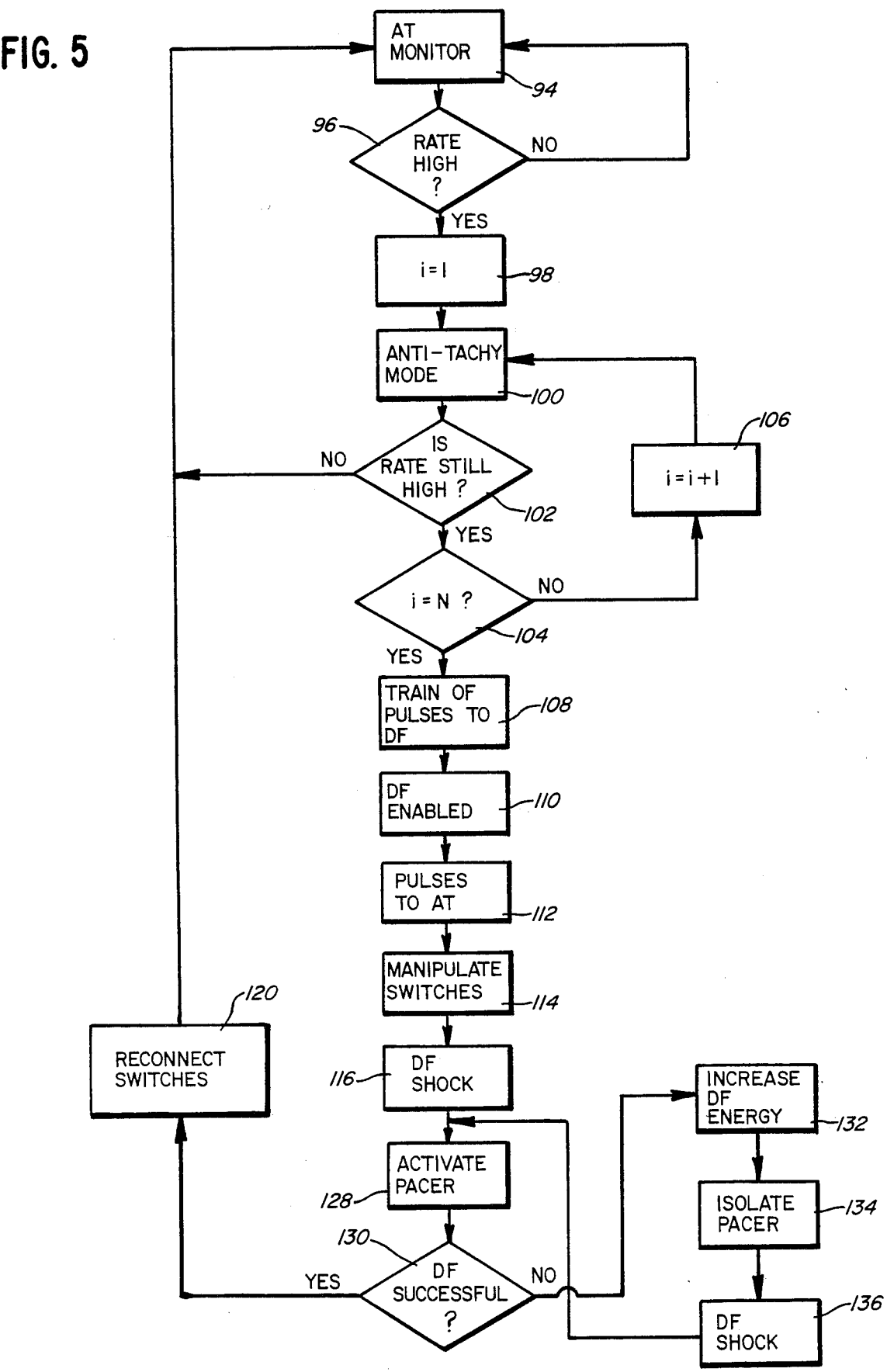
FIG. 5 is a flow chart illustrating the functional steps in the operation of another cardiac stimulation apparatus and method according to the principles of the present invention.

In the embodiment of FIG. 5, steps 94-116 are the same as in the FIG. 4 embodiment just described. However, after the defibrillator issues a shock (116) the pacer is activated (128) by returning the switches to the FIG. 2 position and the pacer performs its analysis to determine if the shock was successful (130). If the shock was not successful, the defibrillator energy is increased (132), the pacer is isolated (134) by returning the switches to their FIG. 3 position, and the defibrillator issues another shock 136. Again the pacer is activated (128) to determine if the shock was successful. If the shock was successful and the arrhythmia is under control, the switches are reconnected (120) to resume monitoring of the heart.

Although an illustrative embodiment of the invention has been shown and described, it is to be understood that various modifications and substitutions may be made by those skilled in the art without departing from the novel spirit and scope of the present invention. For example, the switches illustrated could be implemented by Vemar FETs which draw no power when open. The signal could be emitted from the defibrillation circuit to switch the switches or the signal could be emitted by the pacer circuit or both the pacer circuit and the defibrillation circuit. Although the defibrillator circuit and the pacer may be in a common housing, it is preferred to place them in separate housings because the defibrillator circuit does not last as long as the pacer. In this manner the pacer can remain implanted when the defibrillator circuit is replaced due to battery depletion. It is also desirable that the defibrillator circuit have its own power supply, separate from the pacer's power supply.

What is claimed is:

1. Cardiac stimulation apparatus, which comprises:
   an implantable cardiac pacer having an antitachycardia circuit for GM lowering a patient's electrical heart rate;
   an implantable defibrillator circuit;
   energy source means for said pacer and said defibrillator circuit;
   means for coupling said energy source means to said pacer and defibrillator circuit;
   first means for connecting said pacer to a patient's heart;
   second means for connecting said defibrillator circuit to the patient's heart;
   means coupled to the patient's heart and at least one of said circuits for sensing the patient's electrical heart rate;
   switching means coupled to said first connecting means and said second connecting means, said switching means being operative for isolating the cardiac pacer from the defibrillator circuit during operation of the defibrillator circuit.

2. Cardiac stimulation apparatus as described in claim 1, including means coupled to said sensing means and responsive to said electrical heart rate sensing means for activating said antitachycardia circuit if the electrical heart rate exceeds a predetermined threshold.

3. Cardiac stimulation apparatus as described in claim 2, including means coupled to the defibrillator circuit for activating said defibraillator circuit if said antitachycardia circuit fails to lower the electrical heart rate to below a selected rate.

4. Cardiac stimulation apparatus as described in claim 3, including means coupled to said defibrillator circuit for discontinuing activation of said defibrillator circuit if the patient's electrical heart rate lowers below said selected rate after the defibrillator circuit is activated.

5. Cardiac stimulation apparatus as described in claim 1, including signal means for providing signals between the pacer and the defibrillator circuit for controlling said switching means.

6. Cardiac stimulation apparatus as described in claim 5, said signals comprising a coded pulse train that is transmitted into the patient's tissue via said connecting means.

7. Cardiac stimulation apparatus as described in claim 1, in which said first connecting means comprises an electrical lead from the pacer to the patient's heart.

8. Cardiac stimulation apparatus as described in claim 1, in which said second connecting means comprises an electrical lead from the defibrillator circuit to the patient's heart.

9. Cardiac stimulation apparatus, which comprises:
   an implantable cardiac pacer having an antitachycardia circuit for GM lowering a patient's electrical heart rate;
   an implantable defibrillator circuit;
   energy source means for said pacer and said defibrillator circuit;
   means for coupling said energy source means to said pacer and said defibrillator circuit;
   a first electrical lead from the pacer to the patient's heart;

a second electrical lead from the defibrillator circuit to the patient's heart;

means coupled to the patient's heart and at least one of said circuits for sensing the patient's electrical heart rate;

switching means coupled to said first lead and said second lead, said switching means being operative for isolating the cardiac pacer from the defibrillator circuit during operation of the defibrillator circuit;

means coupled to said sensing means and responsive to said electrical heart rate sensing means for activating said antitachycardia circuit if the electrical heart rate exceeds a predetermined threshold;

means coupled to said defibrillator circuit for activating said defibrillator circuit if said antitachycardia circuit fails to lower the electrical heart rate to below a selected rate;

signal means for providing signals between the pacer and the defibrillator circuit for controlling said switching means, said signals comprising a coded pulse train that is transmitted into the patient's tissue via one of said leads; and means coupled to the defibrillator circuit for discontinuing activation of said defibrillation circuit if the patient's electrical heart rate lowers below said selected rate after the defibrillation circuit is activated.

10. A method for cardiac stimulation which comprises the steps of:

providing an implantable cardiac pacer having an antitachycardia circuit;

providing an implantable defibrillation circuit;

providing energy for said pacer and said defibrillation circuit;

connecting said pacer to a patient's heart;

connecting said defibrillator circuit to a patient's heart;

sensing the patient's electrical heart rate;

if the electrical heart rate exceeds a predetermined rate, then activating said antitachycardia circuit;

if the antitachycardia circuit fails to lower the electrical heart rate to below a selected rate, then isolating the antitachycardia circuit from the defibrillator circuit and thereafter activating said defibrillator circuit.

11. A method as described in claim 10, further comprising providing switching means, said isolating step then comprising the step of providing signals between the pacer and the defibrillator circuit to control said switching means.

12. A method as described in Claim 10, further comprising providing switching means, said isolating step then comprising the step of transmitting a coded pulse train into the patient's tissue to control said switching means.

13. A method as described in claim 10, including the step of transmitting a signal to the defibrillator circuit if the antitachycardia circuit fails to lower the electrical heart rate to below a selected rate.

14. A method as described in claim 10, including the steps of providing switching means for isolating the antitachycardia circuit from the defibrillator circuit; operating the switch means in a first mode to isolate the antitachycardia circuit from the defibrillator circuit and in a second mode to enable the pacer to operate after the defibrillator has provided an appropriate defibrillating voltage.

15. A method for cardiac stimulation which comprises the steps of:

providing an implantable cardiac pacer having an antitachycardia circuit;

providing an implantable defibrillator circuit;

providing energy for said pacer and said defibrillator circuit;

connecting said pacer to a patient's heart;

connecting said defibrillator circuit to a patient's heart;

sensing the patient's electrical heart rate rate;

if the electrical heart rate rate exceeds a predetermined amount, then activating said antitachycardia circuit;

transmitting a signal to the defibrillator circuit if the antitachycardia circuit fails to lower the electrical heart rate rate below a selected amount;

if a signal is transmitted to the defibrillator circuit, then isolating the antitachycardia circuit from the defibrillator circuit and thereafter activating said defibrillator circuit;

providing switching means for isolating the antitachycardia circuit from the defibrillator circuit; and operating the switching means in a first mode to isolate the antitachycardia circuit from the defibrillator circuit and in a second mode to enable the pacer to operate after the defibrillator has provided the appropriate voltage.

* * * * *